United States Patent [19]
Bays

[11] Patent Number: 5,782,795
[45] Date of Patent: Jul. 21, 1998

[54] SURGICAL SUCTION CUTTING INSTRUMENT WITH INTERNAL IRRIGATION

[75] Inventor: F. Barry Bays, Clearwater, Fla.

[73] Assignee: Xomed Surgical Products, Inc., Jacksonville, Fla.

[21] Appl. No.: 497,117

[22] Filed: Jun. 30, 1995

[51] Int. Cl.$^6$ .................................................. A61B 17/20
[52] U.S. Cl. .......................... 604/22; 604/35; 604/43; 606/180
[58] Field of Search ........................ 606/167, 170, 606/180; 604/22, 27, 35, 43, 52, 54

[56] References Cited

U.S. PATENT DOCUMENTS

| Re. 33,258 | 7/1990 | Onik et al. |
|---|---|---|
| 1,636,636 | 7/1927 | Humble . |
| 3,542,031 | 11/1970 | Taylor . |
| 3,732,858 | 5/1973 | Banko . |
| 4,642,090 | 2/1987 | Utrata . |
| 4,708,717 | 11/1987 | Deane et al. ........................ 604/35 |
| 4,909,249 | 3/1990 | Akkas et al. . |
| 4,913,698 | 4/1990 | Ito et al. . |
| 5,084,013 | 1/1992 | Takase . |
| 5,248,297 | 9/1993 | Takase . |
| 5,343,265 | 8/1994 | Mackool . |
| 5,358,473 | 10/1994 | Mitchell . |
| 5,405,348 | 4/1995 | Anspach, Jr. et al. . |

OTHER PUBLICATIONS

"The Wizard Micro Debrider" by Blackstar Instruments, Xomed Surgical Products 6743 Southpoint Drive N., Jacksonville, Florida 32216-0980.

The "Hummer": New Instrumentation for Functional Endoscopic Sinus Surgery, Reuben C. Setliff, III, M.D. & David S. Parsons, M.D.

Linvatec Catalog "IntraArc Small Joint Arthroscopy System", 2 pages.

Stryker Hummer Sales Sheet, 3 pages.

Utilization of a Powered Microdebrider System in Functional Endoscopic Sinus Surgery, Reuben C. Setliff M.D. PC and Davis S. Parsons, M.D., FAAP, FACS, 4 pages.

Primary Examiner—Corrine M. McDermott

[57] ABSTRACT

A surgical suction cutting instrument includes a tubular outer member defining a cutting chamber with an opening, an inner member with a distal cutting edge movably received in the outer tubular member and a flushing mechanism for supplying fluid to the cutting chamber via an outlet communicating with the cutting chamber. The cutting edge of the inner member is disposed within the cutting chamber adjacent the opening to engage bodily tissue through the opening, and a lumen is preferably defined through the inner tubular member in communication with the cutting chamber for aspirating cut bodily tissue. In one embodiment, the flushing mechanism includes a tubular member disposed alongside the outer tubular member and having an outlet communicating with the cutting chamber for supplying fluid to the cutting chamber to prevent and clear clogging of the passage without the need of having to remove the cutting instrument from the surgical site.

21 Claims, 2 Drawing Sheets

SURGICAL SUCTION CUTTING INSTRUMENT WITH INTERNAL IRRIGATION

BACKGROUND OF THE INVENTION

1. Field of the Invention

The present invention relates to surgical cutting instruments and, more particularly, to surgical suction cutting instruments for use in cutting and removing bodily tissue from fluid unavailable surgical sites where irrigation or introduction of fluids is undesirable or proscribed, such as, for example, for use in cutting and removing tissue in the nasal cavity and paranasal sinuses or for use in cutting and removing fibroid tissue or tumors.

2. Discussion of the Prior Art

In many surgical procedures, it is desirable to provide an irrigating fluid to the surgical site to clear bodily fluids, such as blood, and to assist in the removal of cut bodily tissue. In some procedures, such as arthroscopic surgery, it is common for bodily tissue to be cut and removed using surgical suction cutting instruments, such as the Intra-Arc system by Linvatec of Largo, Florida and similar instruments by Smith & Nephew Dyonics of Andover, Massachusetts, and for the irrigating fluid to be provided to the surgical site by separate irrigating instruments developed solely for the purpose of providing irrigation. In other procedures, the irrigating fluid is dispensed from instruments that perform other functions, such as vacuum curettes, as exemplified by U.S. Pat. No. 3,542,031 to Taylor, and No. 5,084,013 and No. 5,248,297 to Takase, powered cutting instruments with suction, as exemplified by U.S. Pat. No. 3,732,858 to Banko, No. 4,909,249 to Akkas et al and No. 5,354,265 to Mackool, and cutting instruments without suction, as exemplified by U.S. Pat. No. 4,642,090 to Utrata, No. 4,913,698 to Ito et al, No. 5,358,473 to Mitchell and No. 5,405,348 to Anspach et al. In the case of surgical suction cutting instruments for use in the eye, such as that described by Banko, the introduction of irrigating fluid also assists in replenishing the material removed from the eye in order to maintain the internal pressure of the eye and to prevent collapse of the retina and related portions.

In procedures involving cutting and removal of bodily tissue from fluid unavailable surgical sites, such as the nasal cavity and paranasal sinuses, irrigation of the surgical site is generally undesirable or prohibited in that some of the irrigating fluid can drain from the surgical site into other areas of the body, such as the lungs, resulting in unwanted complications. For this reason, endoscopic sinus surgery to cut and remove bodily tissue, such as polyps, from the nasal cavity and paranasal sinuses has typically been performed without irrigation using various manually operated and powered (i.e., motorized) cutting instruments.

When used in sinus surgery, manually operated cutting instruments have the disadvantage of tending to rip or tear bodily tissue as the tissue is cut causing unwanted trauma to surrounding mucosal tissue and excessive bleeding. Furthermore, manually operated cutting instruments must typically be withdrawn from the cavity or sinus to remove cut bodily tissue necessitating frequent substitution of instruments and increasing operating time.

Powered cutting instruments for use in sinus surgery, such as the surgical suction cutting instruments known as the Hummer micro-debrider by Stryker Endoscopy of San Jose, Calif. and the BlackStar Wizard micro-debrider by Xomed Surgical Products of Jacksonville, Fla., can reduce operating time by aspirating cut bodily tissue through the lumen of an inner tubular member rotatably received within an outer tubular member. The distal end of the inner tubular member has a surface or edge for engaging tissue via an opening in the distal end of the outer tubular member; and, as the inner tubular member is rotatably driven at its proximal end, for example by a motorized handpiece, the surface or edge of the inner tubular member will cooperate with the opening in the outer tubular member to shear, cut or shave tissue. In use, such powered cutting instruments are usually positioned in the nasal passage with other instruments such as a sinus endoscope; and, as a result, the inner and outer tubular members must be made small enough to maneuver within the limited space of the nasal passage without contacting the other instruments or obstructing the surgeon's view of the surgical site. The small size of the instruments increases the likelihood of cut bodily tissue clogging the lumen of the inner tubular member.

Where the powered suction cutting instrument has no irrigating feature, clogging of cut bodily tissue in the lumen of the inner tubular member frequently occurs requiring that the instrument be removed from the surgical site and dipped in a flushing fluid, such as saline, to clear the lumen of clogged tissue, thereby increasing operating time and the likelihood of blood accumulating at the surgical site. Where the powered cutting instrument has a cannula disposed concentrically around the outer tubular member for self-irrigation, a relatively large portion of the irrigating fluid dispensed by the cannula is deposited at the surgical site. As mentioned previously, in anatomical spaces such as the nasal cavity and paranasal sinuses, irrigation of the surgical site is undesirable or prohibited in that the irrigating fluid can drain from the surgical site into the lungs of the patient causing the patient to drown. Furthermore, it is undesirable to irrigate other fluid unavailable surgical sites during cutting and removal of tissue dependent upon the type and location of the tissue. For example, when removing fibroid tumors during minimally invasive (e.g., laparascopic) procedures, it is desirable to provide irrigation to assist suction removal of cut tissue; however, it is undesirable to irrigate the surgical site in that the irrigating fluid will tend to pool.

SUMMARY OF THE INVENTION

Accordingly, it is a primary object of the present invention to overcome the above mentioned problems and disadvantages associated with using surgical suction cutting instruments at fluid unavailable sites where irrigation is undesirable or prohibited.

It is another object of the present invention to reduce or eliminate the likelihood of cut bodily tissue clogging the lumen of an inner tubular member of a surgical suction cutting instrument without irrigating the surgical site.

It is a further object of the present invention to minimize the amount of fluid needed to reduce or eliminate the likelihood of cut bodily tissue clogging the lumen of an inner tubular member of a surgical suction cutting instrument.

Some of the advantages of the present invention over the prior art are that the present invention allows continuous uninterrupted use of surgical suction cutting instruments, that clogging of surgical suction cutting instruments is reduced or eliminated without irrigating the surgical site, that the amount of fluid used in flushing the surgical suction cutting instrument can be precisely metered or controlled, that the total amount of fluid needed to eliminate clogging of surgical cutting instruments can be minimized, that fluid can be delivered via tubes positioned so as to leave the surgeon's view of the surgical site unobstructed, that fluid can be delivered in pulses to improve flushing of surgical cutting instruments, and that fluid introduced to reduce or eliminate clogging of surgical suction cutting instruments can function as a lubricant thereby increasing the life of the instruments.

The present invention is generally characterized in a surgical suction cutting instrument including a tubular outer member defining a cutting chamber with an opening, an inner member with a distal cutting edge movably received in the tubular outer member and flushing means for supplying fluid to the cutting chamber via an outlet communicating with the cutting chamber. The cutting edge of the inner member is disposed within the cutting chamber adjacent the opening to engage bodily tissue through the opening, and a passage or lumen can be defined through the inner member in communication with the cutting chamber for aspirating cut bodily tissue. In one embodiment, the flushing means includes a tubular member disposed alongside the tubular outer member and having an outlet communicating with the cutting chamber for supplying fluid to the cutting chamber to prevent and clear clogging of the passage without the need of having to remove the surgical suction cutting instrument from the body.

Another aspect of the present invention is generally characterized in a method of cutting and removing bodily tissue at a surgical site including the steps of positioning the bodily tissue within a cutting chamber defined at the distal end of a tubular outer member, cutting the bodily tissue by moving a cutting edge of an inner member within the cutting chamber, aspirating the cut bodily tissue along the inner member, and supplying a fluid to the cutting chamber via an outlet communicating with the cutting chamber.

Other objects and advantages of the present invention will become apparent from the following description of the preferred embodiments taken in conjunction with the accompanying drawings, wherein like parts in each of the several figures are identified by the same reference characters.

DETAILED DESCRIPTION OF THE PREFERRED EMBODIMENTS

The surgical suction cutting instrument of the present invention is described hereinafter as an instrument for cutting and removing bodily tissue from anatomical spaces, such as the nasal cavity and paranasal sinuses, where irrigation of the surgical site is generally undesirable or prohibited. It will be appreciated, however, that the surgical suction cutting instrument of the present invention can be used at any surgical site to cut and remove bodily tissue, including surgical sites where irrigation is permitted or preferred.

Figure 1:
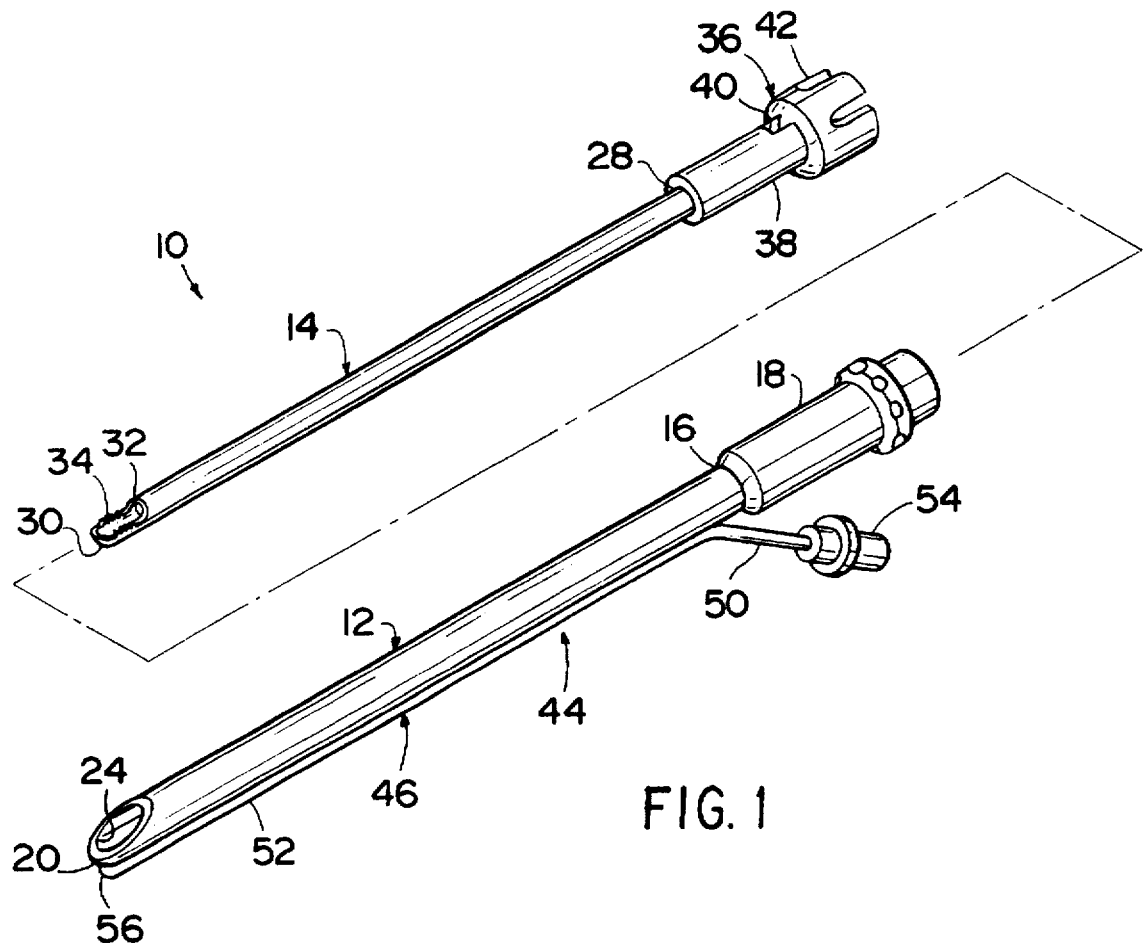
FIG. 1 is an exploded perspective view of a surgical suction cutting instrument according to the present invention.
Figure 2:
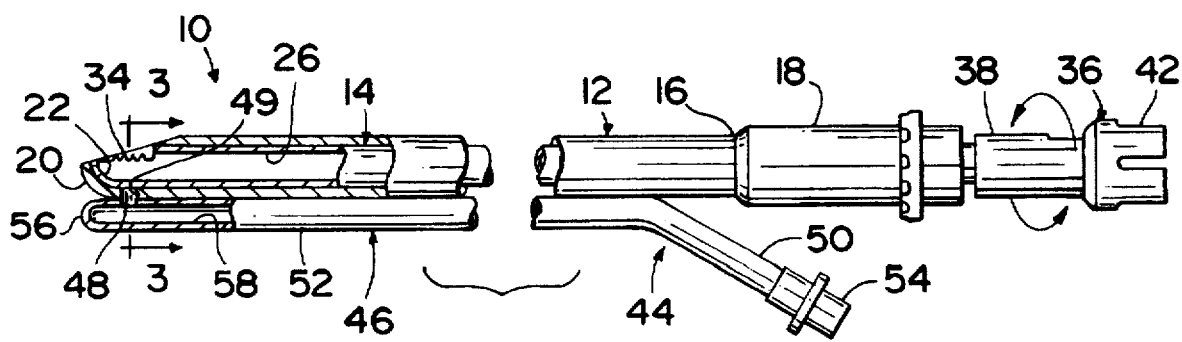
FIG. 2 is a side view, partly in section, of the surgical suction cutting instrument of FIG. 1.

A surgical suction cutting instrument 10 according to the present invention, as illustrated in FIGS. 1 and 2, includes an outer tubular member 12 and an inner tubular member 14 rotatably received in the outer tubular member. Outer tubular member 12 has an open proximal end 16 fixed to a plastic hub 18 and a rounded distal end 20 with a cutting chamber 22 defined therein. An opening 24 at the distal end 20 of the outer tubular member forms a cutting port or window in communication with cutting chamber 22. Inner tubular member 14 defines a lumen 26 between an open proximal end 28 and a distal end 30, the distal end 30 having an opening 32 therein communicating with lumen 26 and forming a suction inlet through which cut bodily tissue can be aspirated. Peripheral edges of opening 32 form a cutting edge 34 at the distal end 30 of the inner tubular member 14, the distal end 30 being positioned within cutting chamber 22 adjacent opening 24 such that the cutting edge 34 can engage bodily tissue through the opening. Proximal end 28 of the inner tubular member 14 is fixed to a plastic hub 36 having a central portion 38 with a transversely extending passage 40 therethrough, the inner tubular member extending through an axial bore in hub 36 to communicate with passage 40. A driven member 42 extends from central portion 38 and is of generally cylindrical configuration with longitudinal slots therein adapted to be driven by a rotating drive shaft of an electric motor in a handpiece. The structure of hubs 18 and 36 is described in brief general terms only since the hubs can be configured for use with any drive system or handpiece capable of rotating or reciprocating an elongate inner tubular member within an elongate outer tubular member to cut or otherwise engage bodily tissue at the distal end and aspirate cut tissue through the lumen of the inner tubular member.

The opening 24 in the distal end of the outer tubular member 12 extends through the side and end walls to produce an edge cooperating with the cutting edge 34 formed on the distal end 30 of the inner tubular member 14 to form a full radius resector. It will be appreciated, however, that the opening 24 can have any desired configuration to cooperate with the configuration of the cutting edge or edges on the distal end of the inner tubular member to cut, shave or trim bodily tissue in or forming an anatomical cavity. Cutting edge 34 on the distal end of the inner tubular member can be smooth or serrated or partly smooth and partly serrated depending upon procedural use and the type of tissue to be removed.

In accordance with the present invention, a flushing mechanism 44 includes an elongate tubular member 46 having an outlet 48 communicating with the cutting chamber 22 via a fluid supply inlet 49 formed in the outer tubular member 12. The tubular member 46 is attached to the outer tubular member 12 and has a proximal portion 50 angled away from a longitudinal axis of the outer tubular member and a distal portion 52 disposed parallel to the longitudinal axis on a side of the outer tubular member opposite opening 24. Proximal portion 50 of the tubular member 46 terminates proximally at a nipple 54 having a configuration to couple with flexible or rigid tubing leading from a fluid source. Distal portion 52 terminates at a closed distal end 56 of generally hemispherical configuration disposed adjacent the distal end 20 of the outer tubular member 12. Outlet 48 is proximally spaced from distal end 56 and is aligned with the fluid supply inlet 49 in the outer tubular member 12 to permit a flushing fluid, such as saline, to flow from a fluid supply channel 58 within tubular member 46 into the cutting chamber 22 defined at the distal end of outer tubular member 12. Fluid supply inlet 49 can be formed anywhere in the outer tubular member 12 in communication with cutting chamber 22 but is preferably formed opposite the cutting port opening 32 and in the path of rotation of the suction inlet formed by opening 32 in the inner member 14. Since the suction inlet formed by opening 32 in the inner member 14 is also in communication with the cutting chamber 22, fluid made to flow from channel 58 of tubular member 46 through the fluid supply inlet 49 and into the cutting chamber 22 will be drawn into the suction inlet formed by opening 32 to be aspirated along with cut bodily tissue through the lumen of the inner member thereby reducing or eliminating clogging of the surgical suction cutting instrument.

Figure 3:
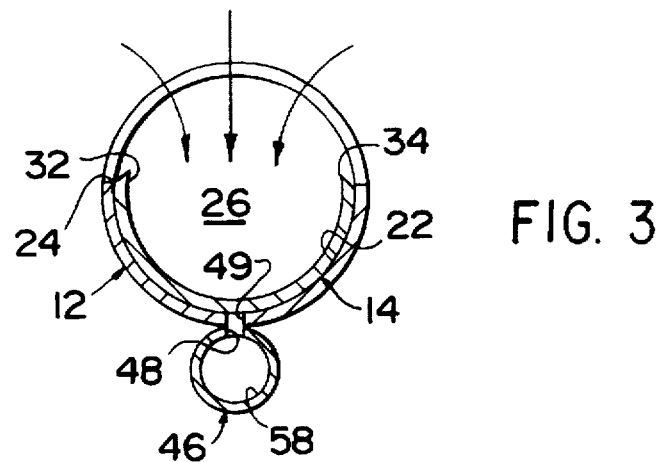
FIGS. 3–5 are sectional views, taken through line 3—3 in FIG. 2, illustrating operation of the surgical suction cutting instrument according to the present invention.
Figure 4:
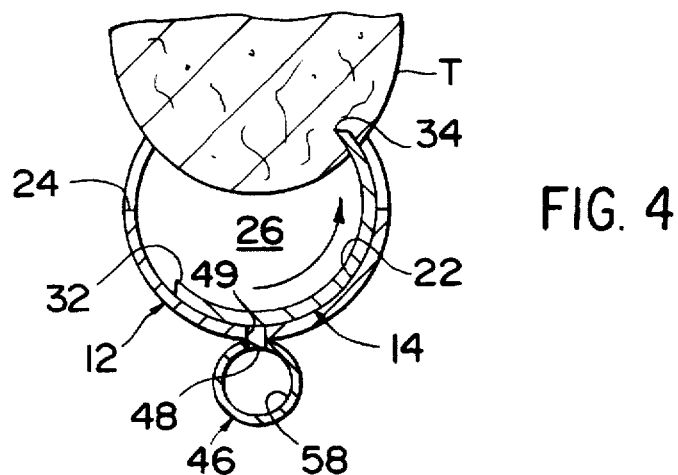
Figure 5:
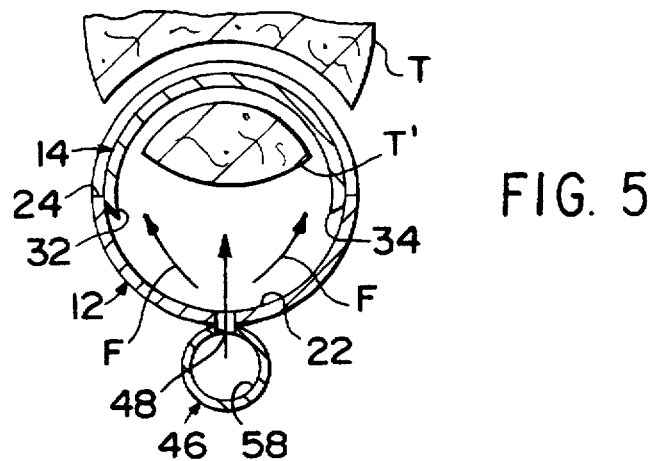

In operation, the inner tubular member 14 is rotatably driven in the outer tubular member 12 such that, when the suction inlet opening 32 and cutting port formed by opening 24 are aligned as shown in FIG. 3, tissue T can be positioned within the cutting chamber 22 via the cutting port formed by opening 24. At the same time, the side of inner tubular member 14 opposite the suction inlet opening 32 will block the fluid supply inlet 49 of the outer tubular member 12 allowing only a small amount of fluid to flow from the tubular fluid supply member 46 into the cutting chamber 22 between the inner and outer tubular members 12 and 14 to serve as a lubricant. With tissue T positioned in the cutting port 24 and fluid supply inlet 49 blocked by the inner tubular member 14, further rotation of the inner tubular member 14 causes cutting edge 34 to engage the bodily tissue T in the cutting port formed by opening 24 as shown in FIG. 4. When the cutting edge 34 has rotated completely through the tissue T, inner tubular member 14 will have rotated about 180° to a position where the cutting port formed by opening 24 is blocked and the fluid supply inlet 49 communicating with the cutting chamber 22 is aligned with the suction inlet formed by opening 32, as shown in FIG. 5. As a result, the fluid supply inlet 49 will no longer be blocked and flushing fluid F will be supplied or introduced into the cutting chamber 22 via the fluid supply inlet 49 to mix with the cut portion T' of the tissue T at the suction inlet formed by opening 32 and to be aspirated through the lumen 26 of the inner tubular member 14 along with the cut bodily tissue to exit the surgical cutting instrument via passage 40 which communicates with a suction passage at the handpiece. In this manner, irrigation of the surgical site is minimized or avoided, and the clogging typically encountered when aspirating cut bodily tissue through the narrow lumen of an inner tubular member is reduced or eliminated such that removal of the surgical cutting instrument from the surgical site for cleaning is not required. Accordingly, operating time can be reduced with the surgical suction cutting instrument of the present invention.

From the above, it will be appreciated that the surgical suction cutting instrument of the present invention permits bodily tissue to be cut and removed at fluid unavailable surgical sites, such as the nasal cavity and paranasal sinuses, where irrigation of the surgical site is undesirable or proscribed by communicating a flushing fluid directly to a cutting chamber formed at the distal end of a tubular outer member for aspiration along an inner member movably received in the tubular outer member. Since the flushing fluid can be precisely administered into the cutting chamber adjacent a suction inlet at the distal end of the instrument, clogging of the instrument by cut bodily tissue can be reduced or eliminated without irrigating the surgical site such that the surgical site is maintained in a dry state. In accordance with the present invention, all or substantially all of the flushing fluid passes directly into the cutting chamber for evacuation with cut tissue; however, for some procedures a small amount of flushing fluid can be tolerated at the surgical site.

Inner and outer members of the surgical suction cutting instrument and the tubular member of the flushing mechanism are preferably made of stainless steel but can be made of any suitable, medical grade materials to permit sterilization for reuse or for single patient use. The tubular member of the flushing mechanism can be positioned at various locations along interior and exterior surfaces of the outer member and can be of various shapes and sizes to define a fluid supply channel having an outlet aligned with a fluid supply inlet formed in the outer member in communication with the cutting chamber. Preferably, the tubular member of the flushing mechanism is of smaller diameter than the outer member and positioned on the side of the outer member opposite the cutting port to provide the surgeon with an unobstructed view of the surgical site. The tubular member of the flushing mechanism can be connected to the outer member by spot welding, adhesive bonding or by any other suitable form of fixation. In addition, the distal end of the tubular member of the flushing mechanism can be rounded as shown, flat or tapered as desired and can terminate adjacent the distal end of the outer member or at locations proximally or distally spaced from the distal end of the outer member so long as there is room to form an outlet leading from the fluid supply channel of the tubular member to a fluid supply inlet communicating with the cutting chamber. The fluid supply inlet communicating with the cutting chamber can be formed anywhere in the tubular outer member so long as the fluid output from the tubular member of the flushing mechanism is communicated into the cutting chamber and the amount of fluid reaching the surgical site is minimized. The fluid supply inlet can have any configuration to form a passage between the fluid supply outlet and cutting chamber including, but not limited to, a single through-hole or slot or a plurality of through-holes or slots. Furthermore, the fluid supply inlet can have any shape to achieve a desired flow pattern and can be oriented at any angle relative to the longitudinal axis of the outer tubular member to form transverse or canted passages between the fluid supply outlet and the cutting chamber. The nipple at the proximal end of the tubular member of the flushing mechanism can have any configuration to couple with fluid supply lines including, for example, tapered configurations with annular ribs, Luer locks or threaded couplings.

The inner member of the surgical suction cutting instrument can be rotatably driven, reciprocated or moved in any other way relative to the tubular outer member by a manually operated mechanism or a powered handpiece. It will also be appreciated that the inner member can have one or more cutting edges formed by a blade, burr or any other type of cutting member depending upon procedural use of the surgical suction cutting instrument and the type of tissue to be removed. The cutting chamber formed at the distal end of the tubular outer member can have any configuration to accommodate the cutting member forming the cutting edge or edges. For example, in the case of a burr, the cutting chamber can be substantially open to permit the burr to contact tissue internally or externally of the chamber.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A method of cutting and removing anatomical tissue at a surgical site comprising the steps of
positioning the anatomical tissue adjacent an opening formed in communication with a cutting chamber at the distal end of a tubular outer member;
cutting the anatomical tissue by moving an inner member having a cutting edge disposed within the cutting chamber only adjacent the opening;

aspirating the cut bodily tissue along the inner member;

conveying a flushing fluid along an exterior of the tubular outer member; and supplying all of the fluid to the cutting chamber via a fluid supply inlet formed through a wall of the outer member in longitudinal alignment with the cutting edge in the cutting chamber so that substantially all of the flushing fluid supplied to the cutting chamber will be aspirated with the cut bodily tissue to reduce clogging without irrigating the surgical site.

2. A method of cutting and removing anatomical tissue comprising the steps of positioning the distal end of a tubular outer member at a fluid unavailable surgical sites positioning the anatomical tissue adjacent a cutting edge at the distal end of an inner member disposed within the tubular outer member;

cutting the anatomical tissue by moving the cutting edge of the inner member within a cutting chamber defined at the distal end of the tubular outer member;

aspirating the cut anatomical tissue along the inner member;

supplying a fluid to the cutting chamber via a fluid supply inlet formed through a wall of the tubular outer member in communication with the cutting chamber.

3. A method of cutting and removing anatomical tissue as recited in claim 2 wherein the fluid unavailable surgical site is a sinus cavity.

4. A method of cutting and removing anatomical tissue at a surgical site comprising the steps of positioning the anatomical tissue adjacent an opening formed in communication with a cutting chamber at the distal end of a tubular outer member;

cutting the anatomical tissue by moving a cutting edge at the distal end of an inner member disposed within the cutting chamber adjacent the opening;

aspirating the cut bodily tissue along the inner member;

conveying a flushing fluid along an exterior of the tubular outer member; and supplying all of the fluid to the cutting chamber via a fluid supply inlet formed through a wall of the outer member in lateral alignment with the cutting edge in the cutting chamber so that substantially all of the flushing fluid supplied to the cutting chamber will be aspirated with the cut bodily tissue to reduce clogging without irrigating the surgical site;

wherein said cutting step includes rotating the inner member relative to the tubular outer member and further comprising the steps of alternatingly blocking and unblocking the fluid supply inlet with the distal end of the inner member to deliver the fluid in pulses.

5. A method of cutting and removing anatomical tissue as recited in claim 4 wherein the inner member defines a lumen with a suction inlet in communication with the cutting chamber and said step of rotating said inner member includes the step of alternatingly aligning the suction inlet with the opening in the cutting chamber and the fluid supply inlet through which the fluid is supplied.

6. A surgical suction cutting instrument comprising a tubular outer member having a proximal end and a distal end, said distal end defining a cutting chamber with an opening;

an inner member having a proximal end, a distal end and a cutting edge disposed at said distal end, said inner member being movably received in said tubular outer member to position said cutting edge within said cutting chamber only adjacent said opening to permit said cutting edge to engage and cut bodily tissue when said inner member is moved;

a lumen defined along said inner member to aspirate cut bodily tissue;

a suction inlet defined at a distal end of said lumen to communicate said cutting chamber with said lumen;

a flushing member defining a fluid supply channel along an exterior of said outer member to convey a flushing fluid; and a fluid supply inlet formed through a wall of said tubular outer member in longitudinal alignment with said cutting edge to communicate all of the fluid conveyed by said fluid supply channel into said cutting chamber so that substantially all of the flushing fluid supplied to said cutting chamber will be aspirated with the cut bodily tissue to reduce clogging without irrigating the surgical site.

7. A surgical suction cutting instrument as recited in claim 6 wherein said flushing member includes a distal portion of tubular configuration with an outlet formed therein in communication with said fluid supply inlet.

8. A surgical suction cutting instrument as recited in claim 7 wherein said outlet is aligned with said fluid supply inlet to transmit fluid from said fluid supply channel to said cutting chamber via said fluid supply inlet.

9. A surgical suction cutting instrument as recited in claim 8 wherein said fluid supply inlet is disposed on a side of said tubular outer member opposite said opening.

10. A surgical suction cutting instrument as recited in claim 9 wherein said tubular distal portion of said flushing member is mounted on a side of said tubular outer member opposite said opening.

11. A surgical suction cutting instrument as recited in claim 10 wherein said tubular distal portion of said flushing member is of smaller diameter than said tubular outer member.

12. A surgical suction cutting instrument as recited in claim 11 wherein a proximal portion of said flushing member is angled away from said tubular outer member.

13. A surgical suction cutting instrument as recited in claim 8 wherein said outlet is formed on a side of said tubular distal portion of said flushing member and a distal end of said tubular distal portion of said flushing member is closed so that any fluid conveyed through said flushing member is directed through said outlet and into said cutting chamber via said fluid supply inlet.

14. A surgical suction cutting instrument as recited in claim 9 wherein said inner member is rotatably movable within said tubular outer member.

15. A surgical suction cutting instrument comprising a tubular outer member having a proximal end and a distal end, said distal end defining a cutting chamber with an opening;

an inner member having a proximal end, a distal end and a cutting edge disposed at said distal end, said inner member being movably received in said tubular outer member to position said cutting edge within said cutting chamber adjacent said opening to permit said cutting edge to engage and cut bodily tissue when said inner member is moved;

a lumen defined along said inner member for aspirating cut bodily tissue;

a suction inlet communicating said cutting chamber with said lumen;

a flushing member defining a fluid supply channel along an exterior of said outer member; and a fluid supply inlet formed in said tubular outer member to communicate said fluid supply channel with said cutting chamber to permit a flushing fluid to be supplied to said cutting chamber without the need of having to remove the instrument from the surgical site;

wherein said lumen and said suction inlet are defined by said inner member, and wherein said opening of said cutting chamber and said fluid supply inlet are alternatingly aligned with said suction inlet as said inner member is moved.

16. A surgical suction cutting instrument as recited in claim 15 wherein said distal end of said tubular outer member is rounded and said opening is formed by a beveled edge at said distal end of said tubular outer member.

17. A surgical suction cutting instrument as recited in claim 15 wherein said distal end of said inner member is configured such that, when said suction inlet is aligned with said opening in said tubular outer member, said fluid supply inlet is substantially blocked by said distal end of said inner member and, when said suction inlet is aligned with said fluid supply inlet, said opening in said tubular outer member is blocked by said distal end of said inner member.

18. A surgical suction cutting instrument comprising a tubular outer member having a proximal end and a distal end, said distal end defining a cutting chamber with an opening;

an inner member having a proximal end, a distal end and a cutting edge disposed at said distal end, said inner member being rotatably received in said tubular outer member to position said cutting edge within said cutting chamber only adjacent said opening to permit said cutting edge to engage and cut bodily tissue as said inner member is rotated;

a lumen defined along said inner member to aspirate cut bodily tissue;

a suction inlet defined at a distal end of said lumen to communicate said cutting chamber with said lumen;

a flushing member defining a fluid supply channel along an exterior of said outer member to convey a flushing fluid; and a fluid supply inlet formed through a wall of said tubular outer member in longitudinal alignment with said cutting edge for communicating all of the fluid conveyed by said fluid supply channel into said cutting chamber so that substantially all of the flushing fluid supplied to said cutting chamber will be aspirated with cut bodily tissue to reduce clogging without irrigating the surgical site.

19. A surgical suction cutting instrument as recited in claim 18 wherein said flushing member defines an outlet in alignment with said fluid supply inlet to transmit fluid from said flushing member to said cutting chamber via said fluid supply inlet.

20. A surgical suction cutting instrument comprising a tubular outer member having a proximal end and a distal end, said distal end defining a cutting chamber with an opening;

an inner member having a proximal end, a distal end and a cutting edge disposed at said distal end, said inner member being rotatable received in said tubular outer member to position said cutting edge within said cutting chamber adjacent said opening to permit said cutting edge to engage and cut bodily tissue as said inner member is rotated;

a lumen defined along said inner member for aspirating cut bodily tissue;

a suction inlet defined at a distal end of said lumen for communicating said cutting chamber with said lumen; and a fluid supply channel defined along said outer member; and a fluid supply inlet formed in said tubular outer member for communicating said fluid supply channel with said cutting chamber to permit flushing fluid to be supplied to said cutting chamber without the need of having to remove the instrument from the surgical site;

wherein said lumen and said suction inlet are defined by said inner member and said opening of said cutting chamber and said fluid supply inlet are alternatingly aligned with said suction inlet as said inner member is rotated.

21. A surgical suction cutting instrument as recited in claim 20 wherein said distal end of said inner member is configured such that, when said suction inlet is aligned with said opening in said tubular outer member, said fluid supply inlet is substantially blocked by said distal end of said inner member and, when said suction inlet is aligned with said fluid supply inlet, said opening in said tubular outer member is blocked by said distal end of said inner member.

* * * * *